United States Patent
Kenley

(10) Patent No.: US 8,562,908 B2
(45) Date of Patent: Oct. 22, 2013

(54) DEVICES, SYSTEMS, AND METHODS FOR CLEANING, DISINFECTING, RINSING, AND PRIMING BLOOD SEPARATION DEVICES AND ASSOCIATED FLUID LINES

(75) Inventor: Rodney S Kenley, Libertyville, IL (US)

(73) Assignees: Baxter International Inc., Deerfield, IL (US); Baxter Healthcare S.A., Glattpark-Opfikon (CH)

( * ) Notice: Subject to any disclaimer, the term of this patent is extended or adjusted under 35 U.S.C. 154(b) by 922 days.

(21) Appl. No.: 11/824,322

(22) Filed: Jun. 29, 2007

(65) Prior Publication Data

US 2009/0004053 A1    Jan. 1, 2009

(51) Int. Cl.
- *A61M 1/00* (2006.01)
- *B01D 65/02* (2006.01)
- *C02F 1/44* (2006.01)

(52) U.S. Cl.
USPC ............... 422/44; 210/240; 210/636; 422/28; 604/6.06

(58) Field of Classification Search
USPC ..................................... 422/44, 28
See application file for complete search history.

(56) References Cited

U.S. PATENT DOCUMENTS

| | | | |
|---|---|---|---|
| 3,753,493 A * | 8/1973 | Mellor | 210/140 |
| 3,871,913 A | 3/1975 | Shaldon | |
| 3,920,030 A | 11/1975 | Mason | |
| 4,552,721 A * | 11/1985 | Fentress et al. | 422/28 |
| 4,695,385 A * | 9/1987 | Boag | 210/636 |
| 4,707,335 A * | 11/1987 | Fentress et al. | 422/44 |
| 4,728,496 A | 3/1988 | Petersen et al. | |
| 5,032,265 A | 7/1991 | Jha et al. | |
| 5,256,371 A | 10/1993 | Pippert | |
| 5,268,144 A | 12/1993 | Heilmann et al. | |
| 5,336,165 A | 8/1994 | Twardowski | |
| 5,591,344 A | 1/1997 | Kenley et al. | |
| 5,651,893 A | 7/1997 | Kenley et al. | |
| 5,674,404 A | 10/1997 | Kenley et al. | |
| 5,714,060 A | 2/1998 | Kenley et al. | |
| 5,725,776 A | 3/1998 | Kenley et al. | |
| 5,783,072 A | 7/1998 | Kenley et al. | |
| 6,044,691 A | 4/2000 | Kenley et al. | |
| 6,132,616 A | 10/2000 | Twardowski et al. | |
| 6,146,536 A | 11/2000 | Twardowski | |
| 6,153,102 A | 11/2000 | Kenley et al. | |
| 6,630,068 B1 * | 10/2003 | Vinci | 210/240 |

FOREIGN PATENT DOCUMENTS

EP          0754468 A     1/1997

* cited by examiner

*Primary Examiner* — Dirk Bass
(74) *Attorney, Agent, or Firm* — McDonnell Boehnen Hulbert & Berghoff LLP

(57) ABSTRACT

Systems and methods for providing for the automatic instrument-based rapid reprocessing of an intact extracorporeal circuit for use in hemodialysis. The system includes a manifold with connectors for engaging a dialyzer as well as venous and arterial blood lines. The manifold is adapted to be moved from a dialysis machine to a reuse instrument without removing the dialyzer and associated blood lines. The system allows for reprocessing of the extracorporeal circuit wherein prior to the next treatment, there is no residual chemical disinfectant requiring testing, the extracorporeal circuit is pre-primed, the levels in the bubble traps are set, and all of the required quality assurance tests are performed and recorded.

12 Claims, 4 Drawing Sheets

DEVICES, SYSTEMS, AND METHODS FOR CLEANING, DISINFECTING, RINSING, AND PRIMING BLOOD SEPARATION DEVICES AND ASSOCIATED FLUID LINES

FIELD OF THE INVENTION

The invention is directed to devices, systems and methods for cleaning, disinfecting or rendering aseptic, rinsing, and priming for reuse medial devices for blood treatment, such as hemodialyzers, hemofilters, and plasmafilters, and their associated fluid lines which may convey blood or other fluids such as saline or heparin.

BACKGROUND OF THE INVENTION

Reuse of hemodialyzers is the standard practice in the field, having been first employed in the mid 1960's. Currently, in the United States, over 80% of all dialysis procedures are preformed with reused. artificial kidneys. Standards for this practice were established by the Association for the Advancement of Medical Instrumentation (AAMI) in the mid 1980's and were later embraced by the Food and Drug Administration who subsequently published their own guidance document regarding dialyzer reuse.

Dialyzer reuse has been necessitated by lack of funding. Federal funding has been decreased in inflation-adjusted dollars by more than 90% since it was enacted in 1972. There are also documented clinical benefits to dialyzer reuse related to the prevention of humoral reactions to the materials of construction of the devices. Some of these reactions, such as acute anaphylaxis, can be lethal.

Reuse of the associated blood tubing sets is also known but much less frequently practiced because of the problems inherent with current reuse practices. When reuse of blood tubing is attempted in a clinical setting, it is only the arterial half of the pair that is reused since clot filtering screens are almost universally present in the bubble traps of the venous line which are very difficult to clean after exposure to blood. The ubiquity of these screens is notwithstanding the complete absence of evidence supporting their utility and the presence of data indicting these components as the source of clot formation on the downstream side of their surface thereby creating the exact problem they are implemented to prevent. Consequently, there are now commercially available venous blood tubing lines which contain no filter screen in the bubble trap and yet others which contain no bubble trap or clot filtering screen.

Reuse may be accomplished either manually, using apparatus designed and built by the dialysis provider, or by automated instruments which are commercially available. Although techniques vary somewhat, through the efforts of AAMI and HCFA (Health Care Finance Administration, now CMS), considerable standardization has occurred. Several quality assurance steps must be taken in order to qualify for federal reimbursement. These include assuring that: the proper concentration of disinfectant is used and that its residence time and duration are adequate, the disinfectant is rinsed out to acceptably low levels prior to the next use, the dialyzer is only used on the same patient, the small molecule transport rate is within 10% of its original value, and the device does not leak.

The various disinfectants that are used include formaldehyde, peracetic acid/hydrogen peroxide, heat, hot citric acid, and glutaraldehydes. Also, bleach and hydrogen peroxide are sometimes employed as oxidizing agents to both cleanse the dialyzers of retained organic material and improve their esthetic appearance. This can be important since the reuse standards stipulate that patients can refuse to reuse a dialyzer for any reason, including its appearance.

The economic pressures on providers of dialysis therapy continue to worsen worldwide as funding continues to be reduced. This is amplified by the continued inflation in labor and operating costs. The result is a continual search on the part of providers to reduce their costs and improve their efficiency. Even with the use of automated equipment, there is still a relatively large labor component attached to each reuse and, as previously noted, in the vast majority of cases only the dialyzer is reused with the blood tubing sets, needles, and IV sets still being discarded with every treatment.

Additionally, prior to each dialysis procedure, a member of the clinic's staff must still spend time assembling new blood tubing sets to the dialyzer, priming the air out of this extracorporeal circuit, setting the correct fluid level in the bubble traps, adjusting the dialysis machine to rinse (dialyze) the disinfectant out of the circuit, and, finally, performing a manual test of the priming solution to assure that the residual disinfectant level is below acceptable limits. In addition, there is a cost to train new employees who are involved in the reuse process and, since there is a fairly high turnover rate for these types of employees, this cost is not insignificant.

It is therefore desirable to provide a method and associated devices which-could reduce the labor and supplies costs of providing dialysis treatments in clinical settings.

U.S. Pat. Nos. 4,552,721 and 4,707,335 to Fentress et al. describes the simultaneous reprocessing of the blood treatment device and its associated and connected blood tubing and other fluid lines without any instrumentation. However, the lack of instrumentation results in the inability to perform the quality assurance tests for small molecule and water transport rates and membrane integrity. Also, the unavailability of high flows and pressures, as can be applied with an instrument, eliminates the opportunity to remove residual organic material by shear forces.

It is therefore desirable to provide a reuse system with instrumentation, in order to provide high flows and pressures.

U.S. Pat. No. 4,695,385 to Boag describes an apparatus which was designed to also allow the simultaneous reprocessing of the dialyzer and associated blood tubing sets while they remained connected to, the dialysis machine. However, this ties up the dialysis machine during the reprocessing procedure, rendering the system non-viable for use in a dialysis clinic where it is necessary to treat multiple patients on the same machine in a day. This system has, therefore, been relegated to home use exclusively.

Similarly, U.S. Pat. No. 6,132,616 to Twardowski et al. describes a system where the dialyzer and connected blood tubing sets (the extracorporeal circuit) remain on the dialysis machine (which doubles as an automated reuse instrument) between treatments as it disinfects not only the extracorporeal circuit, but the dialysate and water purification fluid pathways simultaneously with hot water. Once again, this restricts the use of this system primarily to extra-clinical settings where only one patient will be using the dialysis instrument.

It is therefore desirable to provide a system that reprocesses the dialyzer and associated blood tubing away form the dialysis machine.

In-center hemodialysis is generally performed three times per week for between three and five hours. This means that each hemodialysis machine can treat approximately two cycles of 3-4 patients for a total of 6-8 patients per week. However, it is becoming apparent that daily hemodialysis is the gold standard of care. In this method, hemodialysis is typically performed six days a week for between two to three hours. Daily hemodialysis more closely resembles normal kidney function than treatment three times a week. This means that patients have fewer negative side effects, and may also reduce some of the dietary restrictions and medications for patients.

As discussed above, most artificial kidneys are cleaned, sanitized, and reused. However, the blood tubing is generally not reused. Currently, Medicare as well as commercial insurer payments are based on the three treatments per week. Therefore, daily hemodialysis is not feasible in-center because of the added cost of the incremental blood tubing circuits and the associated time and labor required to set-up and tear-down the extracorporeal circuit between patient shifts. The current reimbursement system, along with the inability to effectively and time-efficiently reuse the venous and arterial blood lines are the main barriers to patients receiving the gold standard of care in clinics. Therefore it is desirable to provide a system that cleans and sanitizes blood tubing for reuse and to do so expediently so that two patient shifts could potentially be performed within approximately the same timeframe as a single shift is currently accomplished including the set-up and tear-down time.

SUMMARY OF THE INVENTION

The invention provides systems and methods for automatically cleaning, disinfecting, and priming a medical device such as a blood separation device.

The system includes a blood separation device having a blood flow path and a dialysate fluid flow path. The system may also include a blood inlet line which delivers blood from the patient to the blood separation device. The system may further include a blood outlet line which returns blood from the blood separation device to the patient. The system may further include a manifold. The manifold may be coupled to the blood separation device. The manifold may include a plurality of connectors for engaging the patient end of the blood inlet line and the blood outlet line. The system may also include a reuse instrument. The manifold may be coupled to the reuse instrument to clean, disinfect, test, and prime the blood inlet and outlet lines and the blood separation device.

Another aspect of the invention provides a method including providing a dialysis machine, a blood separation device, a blood inlet line, a blood outlet line and a manifold. The method may further include coupling the blood separation device to the manifold, the blood inlet and outlet lines to the blood separation device, and the manifold to the dialysis machine. The method may further include connecting the blood inlet and outlet lines to a patient and providing dialysis treatment to the patient.

The method may further include removing the blood inlet and outlet lines from the patient and removing the manifold from the dialysis machine. The method may further include coupling the ends of the blood inlet and outlet lines to the manifold, coupling the manifold to a reuse instrument, and reprocessing the blood inlet and outlet lines and the blood separation device.

Another aspect of the invention provides a method of providing hemodialysis in a clinical setting. The method includes providing a dialysis machine, a reuse instrument, a first patient dialysis set and a second patient dialysis set. The method further includes coupling the first patient dialysis set to the dialysis machine and providing dialysis treatment to a first patient. The method may further include removing the first patient dialysis set from the dialysis machine, coupling the first patient dialysis set to the reuse instrument, and reprocessing the first patient dialysis set.

The method may further include coupling the second patient dialysis set to the dialysis machine and providing dialysis treatment to a second patient. The method may further include removing the first patient dialysis set from the reuse instrument and storing the first patient dialysis. The method may further include removing the second patient dialysis set from the dialysis machine, coupling the second patient dialysis set to the reuse instrument, and reprocessing the second patient dialysis set.

Other features and advantages of the invention shall be apparent based upon the accompanying description, drawings, and claims.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

The current invention provides for the automatic instrument-based rapid reprocessing of the intact extracorporeal circuit 12 where, prior to the next treatment, there is no residual chemical disinfectant requiring testing, the extracorporeal circuit 12 is pre-primed with sterile electrolyte solution supplied by the reuse instrument 72, the levels in the bubble traps 38 if present are set, and all of the required quality assurance tests are performed and recorded. By so doing, much of the residual labor component for setting up each next dialysis treatment is eliminated and the cost of the blood tubing sets 16, 18 is dramatically reduced. Also, the degree of training for reuse technicians is reduced.

Figure 1:
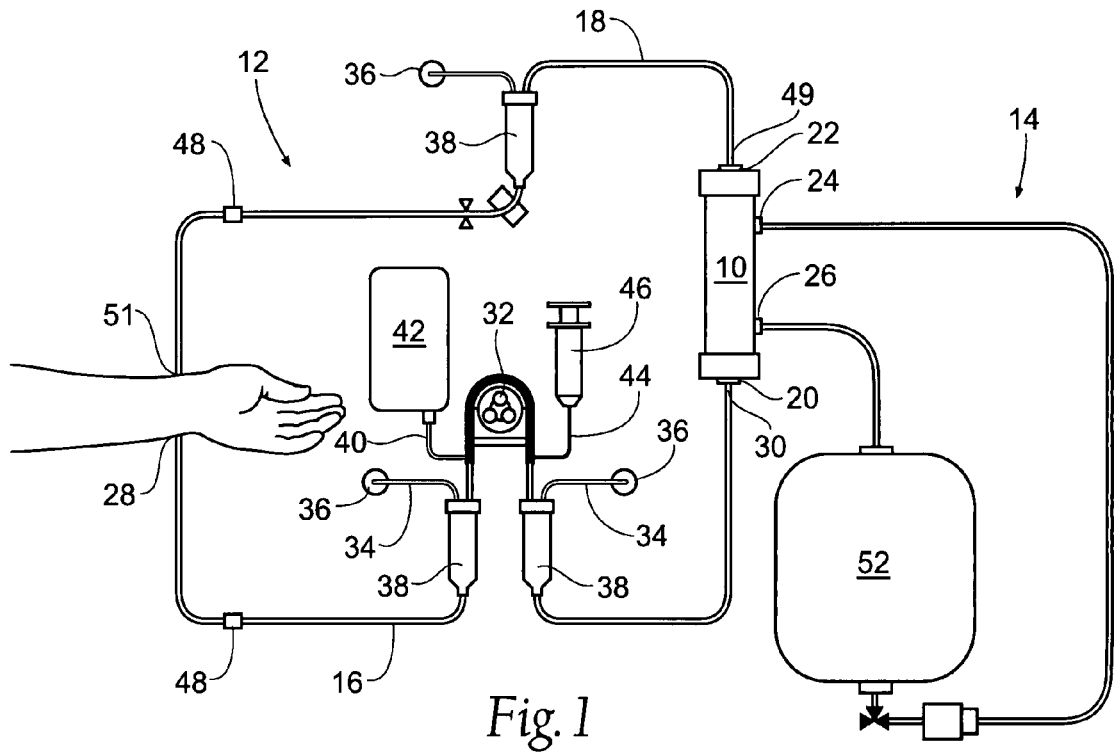
FIG. 1 is a schematic of a general hemodialysis circuit.
Figure 2:
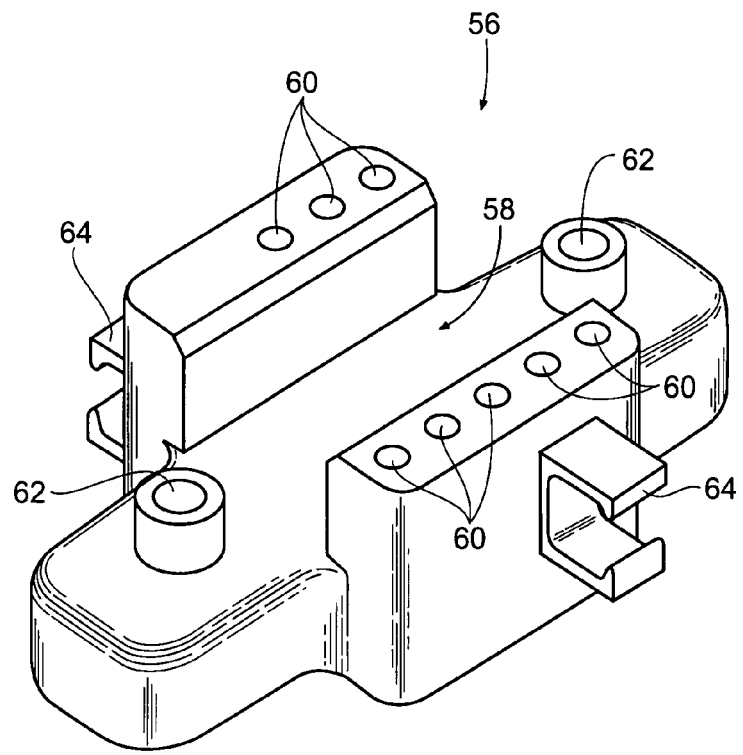
FIG. 2 is perspective view of a manifold according to the present invention.
Figure 3:
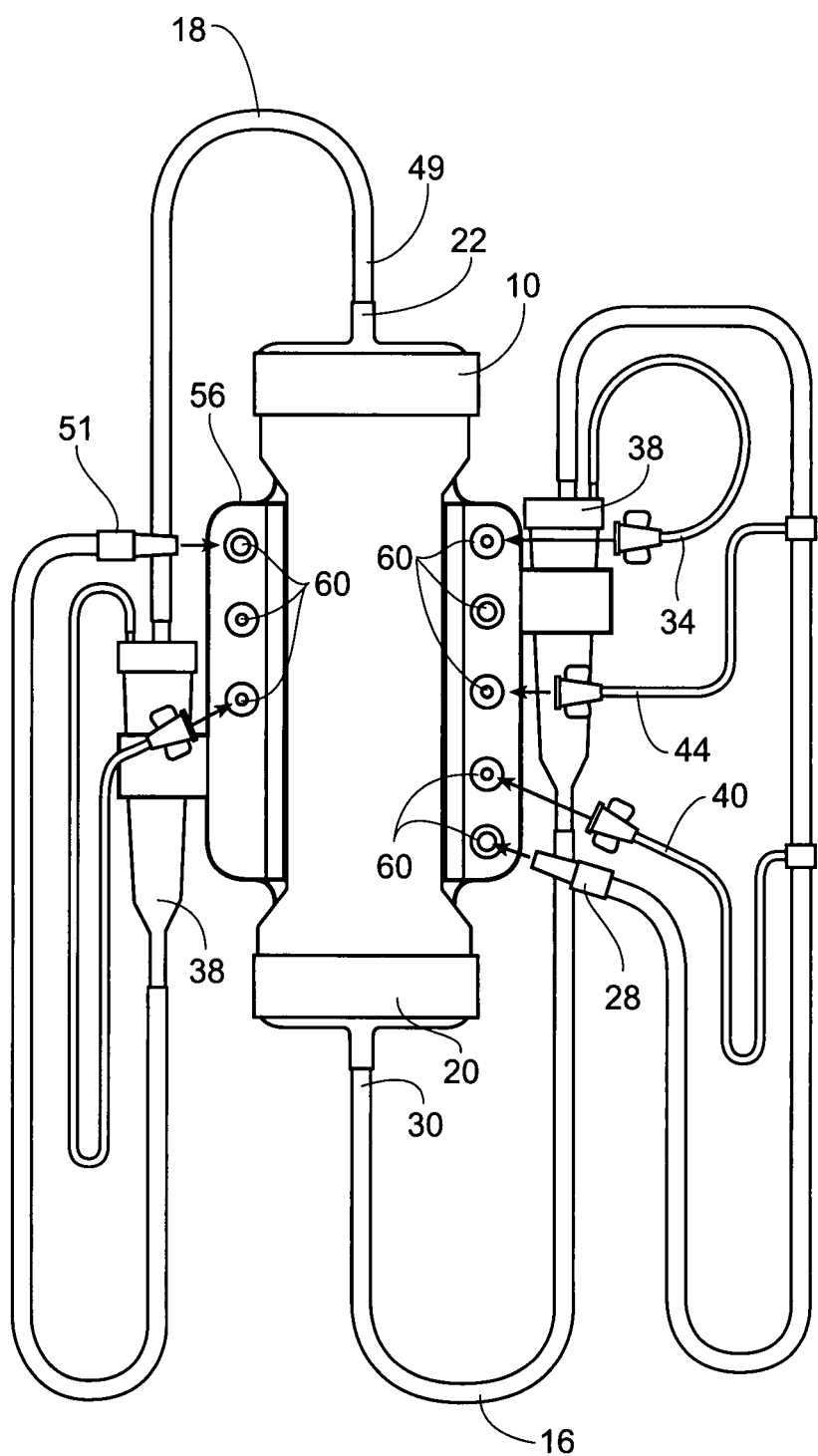
FIG. 3 is a front plan view of the manifold of FIG. 2 coupled to an extracorporeal circuit for use in hemodialysis.
Figure 4:
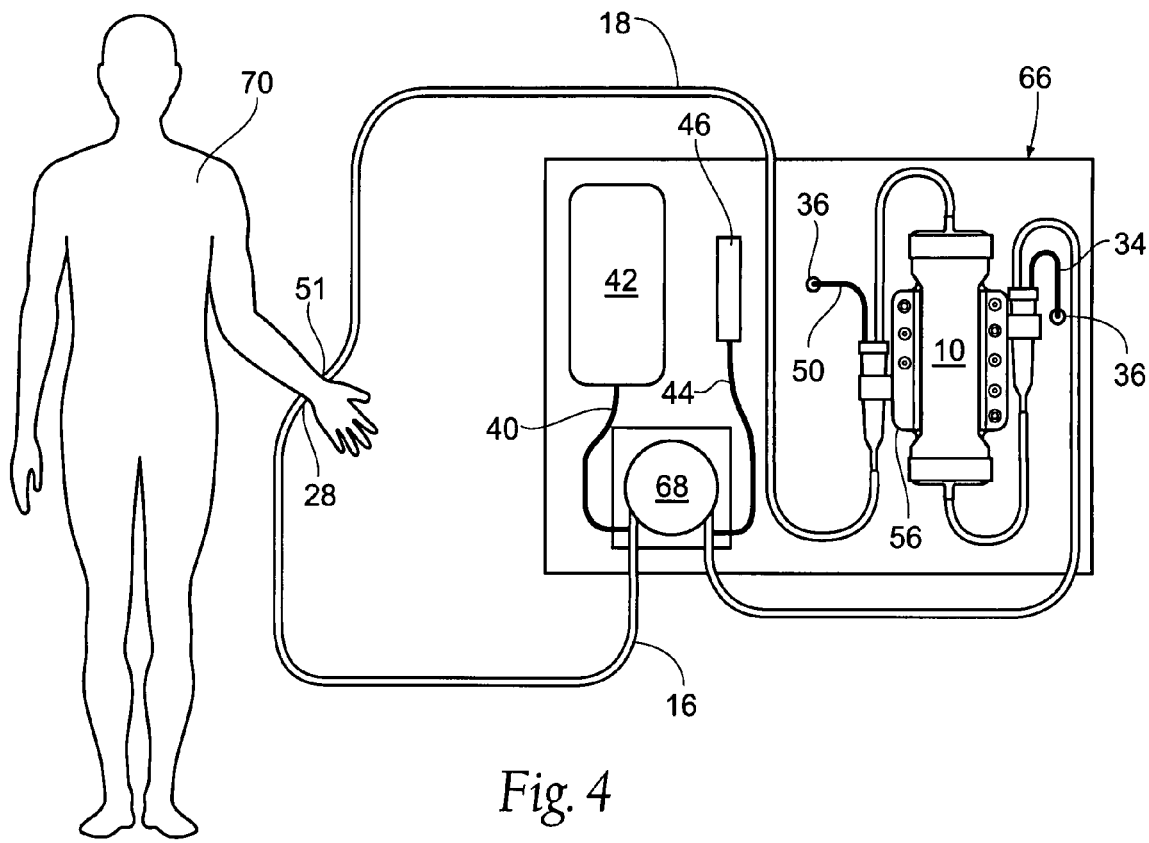
FIG. 4 is a front plan view of the manifold and associated extracorporeal circuit of FIG. 3 coupled to a dialysis machine.

Hemodialysis is a procedure in which a machine filters harmful waste and excess electrolytes and fluid from your blood. FIG. 1 shows a simplified hemodialysis system. Most hemodialysis systems consist of an artificial kidney, also known as a dialyzer 10, connected to an extracorporeal blood circuit 12 and a dialysate circuit 14. The dialyzer 10 is essentially a filter. In the illustrated embodiment the dialyzer 10 generally comprises a case which encloses a bundle of hollow fiber semi-permeable membranes, however any type of filter used in the art could be utilized. The dialyzer 10 is connected to an arterial (inflow) blood line 16 and a venous (outflow) blood line 18. The three components together form an extracorporeal blood circuit. The dialyzer 10 has a blood inlet 20 and a blood outlet 22 as well as a dialysate inlet 24 and a dialysate outlet 26.

The arterial line 16 carries blood from the patient 70 to the dialyzer 10. The arterial line 16 includes a patient end 28 and a device end 30. The patient end 28 is attached to the patient 70 using any type of connection means known in the art. The device end 30 is attached to the inlet 20 of the filter 10 using any type of connection means known in the art. The arterial line 16 generally includes a pump section 32 and at least one side arm 34 leading to a pressure monitor 36. The arterial line 16 may also include at least one air trap 38 associated with the pressure monitor 36. The arterial line 16 may also include a side arm 40 leading to a saline source 42 and/or a side arm 42 leading to an anticoagulant source 46. The arterial line 16 may also include at least one injection site 48 for drawing blood and/or injecting drugs.

The venous line 18 carries the newly dialyzed blood away from the dialyzer 10 and back to the patient 70. The venous line 18 includes a patient end 51 and a device end 49. The patient end 51 is attached to the patient 70 using any type of connection means known in the art. The device end 49 is attached to the outlet 22 of the filter 10 using type of connectors known in the art. The venous line 18 may include at least one side arm 34 leading to a pressure monitor 36. The venous line 18 may further include an air trap 38 associated with the pressure monitor 36.

The dialyzer 10 is also connected to a dialysate circuit 14. The dialysate circuit 14 is well known in the art. In its essence the dialysate circuit 14 includes a dialysate source 52 and a pump 54 to push the dialysate through the filter 10. However, as is known in the art, it is common to find the dialysate source 52 and pump 54 attached to the dialysis machine 66 such that the dialysis process may be monitored.

The present invention generally comprises a system and method for cleaning, disinfecting or rendering aseptic, rinsing, and priming blood treatment devices. The invention preferably comprises a manifold 56 to which the dialyzer 10 may be attached so that all components of the extracorporeal circuit could be transported as a single unit. The manifold 56 is preferably sized and configured such that the dialysate ports 24,26 of the dialyzer 10 and all fluid lines 16,18 of the extracorporeal circuit 12 are connected to the manifold 56 prior to the extracorporeal circuit 12 being removed from the dialysis equipment 66 at the termination of a treatment. The various fluid lines 16,18, including all side arms 34, 40, 44, 50 are then in fluid connection with each other and a reuse instrument 72 in order to clean and prepare the extracorporeal circuit 12 for reuse.

The manifold 56 may include a connector 60 for the patient end 28 of the blood inlet line 16 and the patient end 51 of the blood outlet line 18. The manifold 56 may also include connectors 60 for the ends of any fluid side arms connected to the blood inlet 16 and/or outlet 18 lines. For example, the manifold may include a connector 60 for a saline side arm 40, a connector 60 for a medication sidearm 44, and a connector 60 for the pressure sensing side arms 34, 50. The manifold 56 also preferably includes connectors 62 that communicate with the dialysate inlet 24 and the dialysate outlet 26 located on the dialyzer 10.

The manifold provides fluid communication pathways between each blood line 16,18 and all side arms 34,30,44,50 and the automated reuse instrument 72 to which the manifold 56 may be mated. The manifold 56 may be further designed to provide a fluid communication pathway between the dialysate inlet 24, dialysate outlet 26, and an automated reuse instrument 72 to which the manifold 56 may be mated. It is contemplated that this fluid pathway may be provided by allowing the dialysate inlet 24 and outlet 26 connectors to pass through the manifold 56 and engage the automated reuse machine 72 directly.

It is also contemplated that the manifold 56 may be designed in such a way that when the dialysate inlet 24 and outlet 26 ports of the dialyzer 10 are mated to the manifold 56, fluid egress from the dialysate circuit of the dialyzer 10 is prevented until it is mated with the reuse instrument 72. It is also contemplated that the dialysate inlet 24 and outlet 26 ports of the dialyzer 10 connect to the reuse instrument 72 in the same way that they connect to the dialysis machine 66 (for example, via hoses terminating in Hansen connectors) where the manifold 56 is not involved in this mating at all.

The type of connections 60 used in the manifold 56 would depend on the type of fitting used on the extracorporeal circuit 12. For example, if a male luer connector is used at the patient end 28 of the arterial line 16, the connector 60 in the manifold 56 should be a female luer connector. In this manner the manifold may be design and adapted to fit any available type of tubing circuits 16,18 by simply providing the appropriate number of mating connections 60 for the connections present on the tubing circuits 16,18.

The manifold 56 may also include means 64 to allow the various pieces of tubing 16,18 and bubble traps 38 to be organized in a logical and compact manner. The tubing and bubble traps may be coupled to the manifold using any known means.

In use, the manifold 56 is coupled to the dialyzer 10. The manifold 56 may be coupled to the dialysis machine 66, thus attaching the dialysate circuit 14 to the dialyzer 10. The arterial circuit 16 and the venous circuit 18 are each coupled to the manifold 56 using any type of connector means known in the art. Any side arms 34,30,44,50 may be attached to the appropriate device using any type of connector means known in the art. For example, the pressure monitoring side arms 34,36 are attached to the pressure sensors 36, the saline side arm 40 is attached to the saline source 42, and the anti-coagulant side arm 44 is attached to the anti-coagulant source 46. The extracorporeal blood circuit 12 may then be attached to the patient 70 as is known in the art. The dialysis treatment may then begin.

Figure 5:
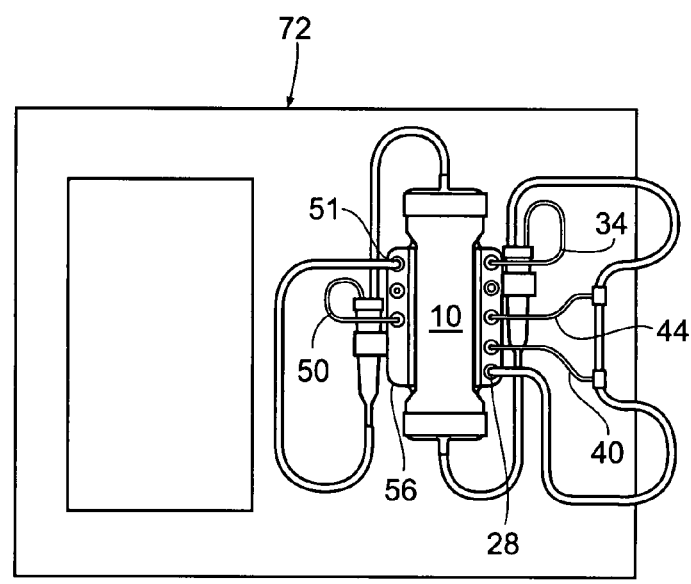
FIG. 5 is a front plan view of the manifold and associated extracorporeal circuit of FIG. 3 coupled to a reuse machine.
Figure 6:
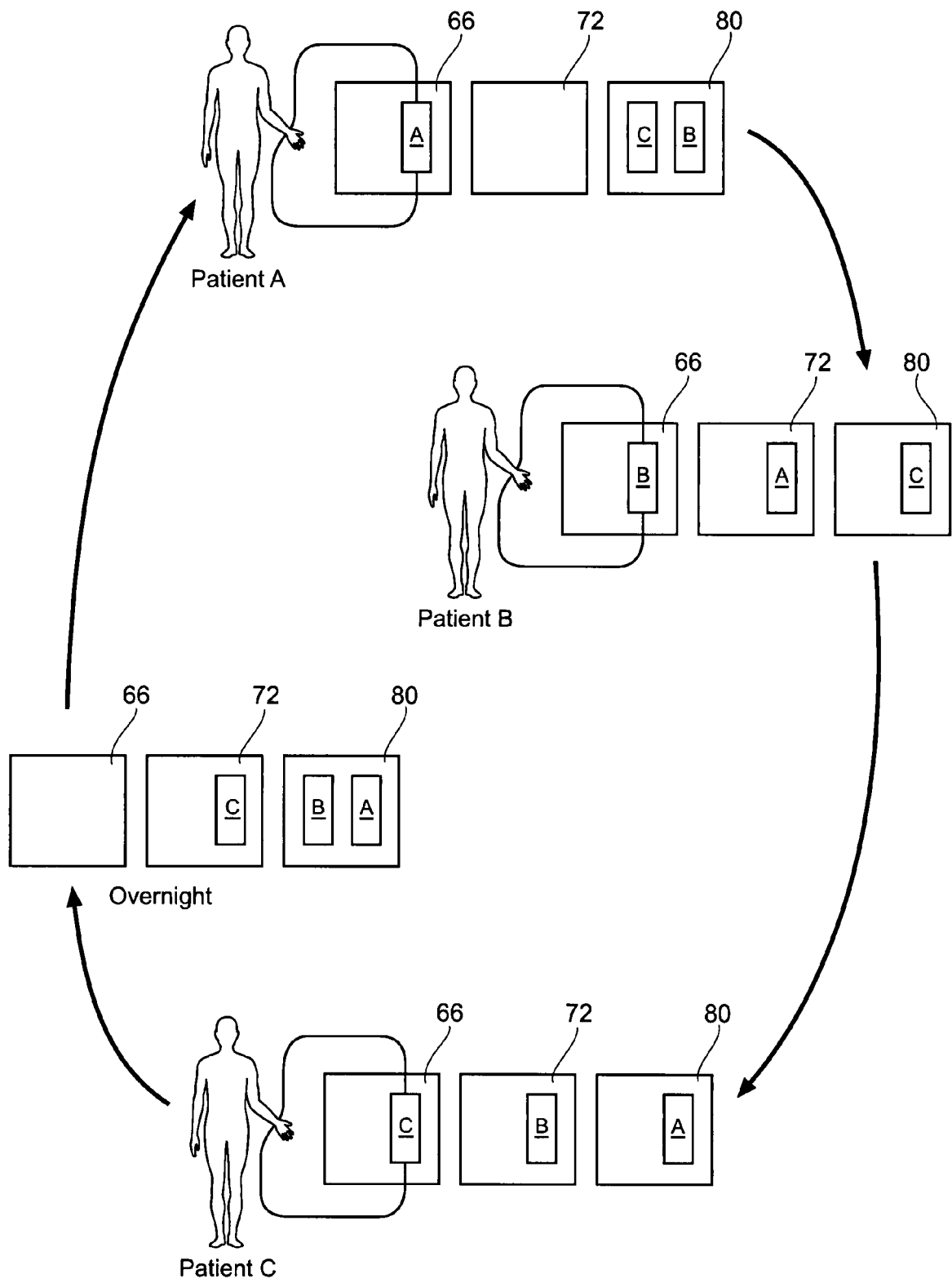
FIG. 6 is a schematic of a method according to the present invention for hemodialysis and reprocessing in a clinical setting.

After dialysis is complete, the venous line 18 and arterial lines 16 are disconnected from the patient 70. The patient end 51 of the venous line 18 is then attached to a connector 60 on the manifold 56 and the patient end 28 of the arterial line 16 is attached to a second connector 60 on the manifold 56. Any additional blood lines, such as venous 50 and arterial 34 pressure monitoring side arms, a saline infusion side arm 40, and a Heparin infusion side arm 44 are also attached to associated connectors 60 on the manifold 56. The manifold 56, including the dialyzer 10 may then be removed from the dialysis machine 66 and placed on a separate reuse instrument 72, as shown in FIG. 5. The manifold 56 is preferably sealingly mated to the reuse instrument 72. Preferably, the dialysate inlet 24 and outlet engage 26 the reuse instrument 72 when the manifold 56 is placed on the reuse instrument 72. The reuse instrument 72 will then process both the dialyzer 10 and the associated arterial line 16 and venous line 18.

In one embodiment, the fluid paths integral to the manifold 56 may be designed in such a way so as to prevent any further fluid egress once the various connections of the extracorporeal circuit are made to it. One method of accomplishing this would be to terminate the fluid paths integral to the manifold 56 on the side which will mate to the reuse instrument 72 in female needleless connectors. Needleless connectors are well known in the art (e.g. U.S. Pat. No. 5,100,394) and typically consist of a male and female counterpart where the female counterpart is typically an injection site where the elastomeric septum (e.g. latex or silicone rubber) is pre-split and compressed in a housing such that a blunt male cannula (as opposed to a sharp needle) may penetrate the septum to accomplish injection or removal of a fluid while still assuring that there is complete sealing around the male cannula. The female needleless injection site termination points on the manifold 56 may then mate to blunt male cannula counterparts on the reuse instrument 72 such that when the manifold 56 is pushed onto the reuse instrument 72; the fluid pathways internal to the manifold 56 are accessed allowing all fluid pathways of the extracorporeal circuit to also be accessed by the reuse instrument 72. When the reuse process is complete and the extracorporeal circuit/manifold assembly is removed by pulling it away from the reuse instrument 72, the female needleless injection sites instantly close preventing leakage of the sterile electrolyte solution contained therein. A similar design could be used in the connection of the dialyzer dialysate ports 24,26 to the reuse instrument 72.

It should also be understood that some inlet 16 and outlet 18 blood lines may contain no bubble traps 38 or side arms 34,40,44,50 of any kind. In this case, there may be no need for a manifold 56 to accomplish the method of extracorporeal circuit reuse herein described. Conventional blood tubing sets for hemodialysis are typically sold with a recirculation connector included in the sterile package. This recirculation connector allows for the patient ends 28,51 of the arterial 16 and venous 18 blood lines to be connected together prior to the start of a clinical treatment so that any residual disinfectant or priming solution may be recirculated through the entire extracorporeal circuit under the control of the dialysis machine 66 thereby allowing residual contaminants to be dialyzed away. This same recirculation connector could be employed at the end of a clinical treatment to once again connect the patient ends 28,51 of the arterial 16 and venous 18 blood lines together to insure no egress of fluid as the extracorporeal circuit is removed from the dialysis machine 66 and transported to the reuse instrument 72. Connection to the reuse instrument 72 in this case could be as simple as connecting the dialyzer's dialysate inlet 24 and outlets 26 ports to connectors on the reuse machine 72 that are identical to those on the dialysis machine 66 (e.g. hoses terminating in Hansen connectors) and the patient end connectors (male luers) of the two blood lines 16,18 could be inserted into mating counterparts on the reuse instrument 72 once disconnected from the recirculation connector. The connection of the blood lines 16,18 to the reuse instrument 72 would preferably be locked in such a way to prevent these lines from blowing off of the reuse instrument 72 under the positive pressure that would typically be used to introduce fluid into the blood lines 16,18.

It should be understood that a closed blood circuit is formed by use of either the manifold or recirculation connector. It is further contemplated that the closed blood circuit may be formed by any means known in the art. For example, the closed blood loop may be created by closing a clamp near the patient ends 28,51 of both the arterial 16 and venous 18 blood lines.

The automated reuse instrument 72 may control the passage of various fluids through all of the fluid pathways of the manifold 56 in an automated manner in order to clean and disinfect the extracorporeal circuit 12. The entire extracorporeal circuit 12 may be tested for leaks by the instrument 72. The instrument 72 may also measure the solute transport rate of the dialyzer 10, set the level of the bubble traps 38, leave the extracorporeal circuit primed with sterile electrolyte solution for the next treatment, and record, store, export and display all required quality assurance data. This reduces the amount of time it takes to prepare for a next dialysis session and allows the degree of training for reuse technicians to be reduced.

It should also be understood that the extracorporeal circuit may be manually primed, off-line from the reuse instrument 72, at any point in time prior to treatment. If the extracorporeal circuit is primed off-line, it would be preferable to do immediately prior to treatment to avoid contamination of the electrolyte solution.

It should also be understood that the system and methods described herein allow for the reprocessing of the intact extracorporeal circuit 12, including the venous segment 18, offline from the dialysis machine 66 by a separate automated instrument 72. This system and method allows the venous 18 and arterial 16 lines of the extracorporeal circuit 12 to be reused which not only makes daily hemodialysis feasible in a clinical setting, but also reduces the cost of standard three times a week treatment.

For a single patient receiving dialysis treatment three times a week, a clinic currently would need to utilize 156 sets of venous 18 and arterial 16 lines per year. For daily treatment, this number jumps to 312 sets of venous 18 and arterial 16 lines per year. Using the systems and methods described herein, the clinic may use a single extracorporeal circuit 12 for each patient for 30 or more uses. This results in approximately 10-11 extracorporeal circuits 12 being used per year for each patient for daily treatment and 5-6 extracorporeal circuits 12 per year for three times a week treatment. This is a savings of 150-300 sets of venous 18 and arterial 16 lines per year for a single patient.

Further, because a new set of arterial 16 and venous 18 lines do not have to be attached to the dialyzer 10 prior to each dialysis treatment, there is reduced labor associated with the dialysis process. This may further also result in fewer chances of user error (e.g. touch contamination of the sterile fluid path) because the blood lines 16,18 do not have to be reattached prior to each use.

It should be understood that the systems and methods of this invention may be particularly useful in a clinical setting. A clinic may have a single dialysis machine 66 and a single reuse instrument 72. For each patient the clinic could then utilize an individual dialysis set comprising a complete extracorporeal circuit 12, including a dialyzer 10, coupled to a manifold 56. Each dialysis set is preferably specifically designated for use with a single patient. For example, if the clinic treats three patients, the clinic would have patient dialysis set A for patient A, patient dialysis set B for patient B, and patient dialysis set C for patient C.

Patient A may receive dialysis using patient dialysis set A attached to the dialysis machine 66 in the manner described above. After patient A's dialysis treatment is complete, patient dialysis set A is removed from the dialysis machine 66 and attached to the reuse instrument 72 for reprocessing. While patient dialysis set A is being reprocessed, patient dialysis set B may be attached to the dialysis machine 66 and patient B may receive dialysis treatment. After patient B's dialysis treatment is complete, patient dialysis set A is removed from the reuse instrument 72 and placed in storage 80 for patient A's the next treatment. Patient dialysis set B is then removed from the dialysis machine 66 and attached to the reuse instrument 72 for reprocessing. While patient dialysis set B is being reprocessed, patient dialysis set C may be attached to the dialysis machine 66 and patient C may receive dialysis treatment. After patient C's dialysis treatment is complete, patient dialysis set B is removed from the reuse instrument 72 and placed in storage 80 for patient B's the next treatment. Patient dialysis set C is then removed from the dialysis machine 66 and attached to the reuse instrument 72 for reprocessing. If patient C is the final patient of the day, patient dialysis set C may be left on the reuse instrument 72 overnight. The next morning, patient dialysis set C may be removed from the reuse instrument 72 and placed in storage 80 for patient C's next treatment. If patient C is not the final patient of the day, the method would continue as described above for additional patients.

It should be understood that the clinic could treat any number of patients without departing from the principals of the present invention. Regardless of the number of patients treated, each patient's dialysis set may be removed from the dialysis machine 66 after use and reprocessed on the reuse instrument 72 prior to the patient's next treatment. In this manner the clinic may be simultaneously treating one patient while reprocessing a different patient's dialysis set, thus increasing the number of patients the clinic can treat each day. Further, because the extracorporeal circuit 12 always remains attached to the manifold 56 through the dialyzer 10, and the venous 18 and arterial circuits 16 are not disconnected from the dialyzer 10 after each use, the efficiency of the clinic may be increased due to a decrease in labor to assemble and disassemble the extracorporeal circuit 12 from the dialyzer 10 for each patient treatment.

It should be understood that the types of connectors 60 used on the manifold 56 may be changed without departing from the invention. It should further be understood that the configuration and number of connectors 60,62 is based on the type of arterial 16 and venous 18 lines and the dialyzer 10 being used and could be changed in order to adapt the manifold 56 to be used with any type of arterial 16 and venous 18 lines and dialyzer 10 that may be available now or in the future.

For example, inlet (arterial) 16 and outlet (venous) 18 blood lines are known in the art that contain no air traps 38 or side arms 34,40,44,50. In this case, the only connections from the blood lines 16,18 into the manifold 56 would be the patient end connectors 28,51 such that once connected, no residual fluid contained in the extracorporeal circuit could thereafter drip out. Even in this case, as described previously, the manifold 56 serves as an organizer for the blood lines 16,18 and dialyzer 10 to be conveniently and quickly transported as one unit from the dialysis machine 66 to the reuse instrument 72 without the danger of possibly contagious patient blood leaving the blood flow path. It also provides a convenient and rapid attachment method to the reuse machine 72.

It is also contemplated that the same instrument 72 and associated components may be used to affect automated priming of the extracorporeal circuit 12 with sterile electrolyte solution prior to treatment. This further simplifies the reuse process and reduces the amount of labor necessary.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A system for automatically cleaning, disinfecting, testing, and priming an extracorporeal blood circuit for reuse in a dialysis machine comprising:
   (a) an extracorporeal blood circuit incorporated in a dialysis machine, the extracorporeal circuit comprising:
      a blood separation device, said blood separation device having a blood flow path, a semipermeable membrane, and a second fluid flow path separated from the blood flow path by the semipermeable membrane, the blood flow path having a blood inlet and a blood outlet, and the blood separation device having at least one port in fluid communication with the second fluid flow path;
      a blood outlet line, the blood outline line having a device end and at least one patient end, the device end being sized and configured for engagement with the blood separation device blood outlet;
      a blood inlet line, said blood inlet line having a device end and at least one patient end, the device end being sized and configured for engagement with the blood separation device blood inlet;
      a manifold, said manifold being sized and configured for engagement with the blood separation device, the manifold having a plurality of blood line connectors, at least one port connector, and at least one reuse connector, wherein the blood line connectors are sized and configured for engagement with one or more patient ends of the blood inlet line and the blood outlet line; and the at least one reuse connector is sized and configured for fluid communication with at least one of the blood line connectors; and the port connector is sized and configured for engagement with the port of the second fluid flow path of the blood separation device; and
   (b) a reuse instrument for automatically cleaning, disinfecting, testing and priming the extracorporeal blood circuit, said reuse instrument being configured to connect with the manifold through a first fluid connection with the at least one reuse connector and a second fluid connection with the at least one port connector, wherein the manifold is attached to the blood separation device and wherein the blood separation device, blood outlet line, blood inlet line and manifold are removable from the dialysis machine as a single unit following use for separate processing by the reuse instrument; and wherein the reuse instrument is adapted to cause fluid transport across the semipermeable membrane of the blood separation device via the first and second fluid connections.

2. The system of claim 1 wherein said blood inlet line includes at least one sidearm, said side arm including a free end; and said manifold includes at least one connector sized and configured for engagement with the free end of the at least one blood inlet line side arm; wherein said manifold provides a fluid communication pathway between the blood inlet line and the side arm.

3. The system of claim 1 wherein said blood outlet line includes at least one side arm, said side arm including a free end; and said manifold includes at least one connector sized and configured for engagement with the free end of the at least one blood outlet line side arm; wherein said manifold provides a fluid communication pathway between the blood outlet line and the side arm.

4. The system of claim 1 wherein said reuse instrument is further adapted to disinfect the blood inlet line, the blood outlet line, and the blood separation device.

5. The system of claim 1 wherein said reuse instrument is further adapted to prime the blood inlet line, the blood outlet line, and the blood separation device.

6. The system of claim 1 wherein said reuse instrument is further adapted to test the blood inlet line, the blood outlet line, and the blood separation device for leaks.

7. A method comprising:
   providing a dialysis machine;
   providing an extracorporeal blood circuit incorporated in a dialysis machine, the extracorporeal circuit comprising:

a blood separation device, said blood separation device having a blood flow path, a semipermeable membrane, and a second fluid flow path separated from the blood flow path by the semipermeable membrane, the blood flow path having a blood inlet and a blood outlet, and the blood separation device having at least one port in fluid communication with the second fluid flow path;

a blood outlet line, the blood outlet line having a device end and at least one patient end, the device end being sized and configured for engagement with the blood separation device blood outlet;

a blood inlet line, the blood inlet line having a device end and at least one patient end, the device end being sized and configured for engagement with the blood separation device blood inlet;

a manifold, said manifold being sized and configured for engagement with the blood separation device, the manifold further having a plurality of blood line connectors, at least one port connector, and at least one reuse connector, wherein the blood line connectors are sized and configured for engagement with one or more patient ends of the blood inlet line and the blood outlet line; the at least one reuse connector is sized and configured for fluid communication with at least one of the blood line connectors; and the port connector is sized and configured for engagement with the port of the second fluid flow path of the blood separation device;

providing a reuse instrument for automatically cleaning, disinfecting, testing and priming the extracorporeal blood circuit, said reuse instrument being configured to connect with the manifold through a first fluid connection with the at least one reuse connector and a second fluid connection with the at least one port connector;

coupling the blood separation device to the manifold;

coupling the blood inlet line to the blood separation device blood inlet;

coupling the blood outlet line to the blood separation device blood outlet;

coupling the manifold to the dialysis machine;

coupling the patient end of the blood inlet line and the blood outlet line to a patient;

providing dialysis treatment to a patient;

removing the manifold from the dialysis machine following the dialysis treatment; and coupling the manifold to a reuse instrument for reprocessing for reuse, wherein the manifold is attached to the blood separation device and wherein the blood separation device, blood outlet line, blood inlet line and manifold are removable from the dialysis machine as a single unit following use for separate processing by the reuse instrument; and wherein the reuse instrument is adapted to cause fluid transport across the semipermeable membrane of the blood separation device via the first and second fluid connections.

8. The method of claim 7 wherein prior to said removing the manifold, further comprising removing the patient end of the blood inlet line and the blood outlet line from the patient; and coupling the patient end of the blood inlet line and blood outlet line to the manifold connectors.

9. The method of claim 8 wherein said reprocessing further comprises cleaning the blood inlet line, blood outlet line, and blood separation device.

10. The method of claim 9 further comprising disinfecting the blood inlet line, blood outlet line, and blood separation device.

11. The method of claim 9 further comprising priming the blood inlet line, blood outlet line, and blood separation device.

12. The method of claim 9 further comprising testing the blood inlet line, blood outlet line, and blood separation device for leaks.

* * * * *